(12) United States Patent
Bathen et al.

(10) Patent No.: US 10,605,753 B2
(45) Date of Patent: Mar. 31, 2020

(54) DEVICE AND METHOD FOR CALORIMETRICALLY MEASURING SORPTION PROCESSES

(71) Applicant: Waters GmbH, Eschborn (DE)

(72) Inventors: Dieter Bathen, Duisburg (DE); Tatjana Hayn, Duisburg (DE); Cornelia Will, Bochum (DE); Frieder Dreisbach, Witten (DE)

(73) Assignee: WATERS GMBH, Eschborn (DE)

( * ) Notice: Subject to any disclaimer, the term of this patent is extended or adjusted under 35 U.S.C. 154(b) by 1018 days.

(21) Appl. No.: 14/381,946

(22) PCT Filed: Feb. 14, 2013

(86) PCT No.: PCT/EP2013/052998
§ 371 (c)(1),
(2) Date: Aug. 28, 2014

(87) PCT Pub. No.: WO2013/127642
PCT Pub. Date: Sep. 6, 2013

(65) Prior Publication Data
US 2015/0072437 A1    Mar. 12, 2015

(30) Foreign Application Priority Data
Feb. 28, 2012  (DE) .......................... 10 2012 101 621

(51) Int. Cl.
*G01N 25/38*    (2006.01)
*G01N 25/48*    (2006.01)
(Continued)

(52) U.S. Cl.
CPC ........... *G01N 25/482* (2013.01); *G01K 17/06* (2013.01); *G01K 19/00* (2013.01);
(Continued)

(58) Field of Classification Search
CPC ............. G01N 25/482; G01N 25/4866; G01N 25/4893; G01N 25/4873; G01K 19/00; G01K 17/06
(Continued)

(56) References Cited

U.S. PATENT DOCUMENTS

| | | | |
|---|---|---|---|
| 4,761,078 A | 8/1988 | Farris et al. | |
| 5,295,745 A * | 3/1994 | Cassettari | G01N 25/4866 374/10 |
| 8,501,092 B2 * | 8/2013 | Gimzewski | G01K 1/16 422/51 |

FOREIGN PATENT DOCUMENTS

| | | |
|---|---|---|
| DE | 200 11 022 U1 | 12/2000 |
| JP | 50-015595 A | 2/1975 |

(Continued)

OTHER PUBLICATIONS

English Translation of International Preliminary Report on Patentability (6 pages) Sep. 12, 2014.
(Continued)

*Primary Examiner* — Rebecca M Fritchman
(74) *Attorney, Agent, or Firm* — Schmeiser, Olsen & Watts LLP

(57) ABSTRACT

The aim of the invention is to provide a commercially usable and inexpensive device and method with which a sorption enthalpy can be measured in a simple manner. This is achieved by a device for calorimetrically measuring sorption processes, comprising a sorption cell for receiving a sample, the sorption cell having a volume for filling with a sorption gas, and comprising a reference cell likewise for filing with the sorption gas. A measurement gas volume is arranged around the sorption cell for receiving a reference gas, and the reference cell is surrounded by a reference gas volume, which is likewise provided for receiving the reference gas. A gas connection is provided between the sorption cell and
(Continued)

the reference cell in order to conduct sorption gas into the sorption cell and the reference cell such that a sorption reaction occurs with the sample in the sorption cell. Furthermore, a device is provided for measuring pressure differences between the measurement gas volume and the reference gas volume in order to carry out a calorimetric measurement of the sorption process on the sample in the sorption cell on the basis of a volume change of the reference gas in the measurement gas volume.

10 Claims, 2 Drawing Sheets

(51) Int. Cl.
*G01K 17/06* (2006.01)
*G01K 19/00* (2006.01)
(52) U.S. Cl.
CPC ..... *G01N 25/4866* (2013.01); *G01N 25/4873* (2013.01); *G01N 25/4893* (2013.01)
(58) Field of Classification Search
USPC ............................................ 436/147; 422/51
See application file for complete search history.

(56) References Cited

FOREIGN PATENT DOCUMENTS

| | | |
|---|---|---|
| JP | 10503013 A | 3/1998 |
| JP | 3055705 U | 1/1999 |
| JP | 2001330519 A | 11/2001 |
| JP | 2003240743 A | 8/2003 |
| WO | WO 96002826 A1 | 2/1996 |

OTHER PUBLICATIONS

I. Wadso et al., "A New Method for Determination of Vapour Sorption Isotherms Using a Twin Double Microcalorimeter," Thermochimica Acta 271, pp. 179-187 (1996).
International Search Report for Counterpart PCT/EP2013/052998 (2 pages) dated May 22, 2013.
English Translation of Japanese Notification of Reason for Refusal in counterpart Japanese Application No. 2014-558071 dated Oct. 11, 2016 (3 pages).

\* cited by examiner

DEVICE AND METHOD FOR CALORIMETRICALLY MEASURING SORPTION PROCESSES

BACKGROUND OF THE INVENTION

Field of the Invention

The invention relates to a device and a method for calorimetrically measuring sorption processes.

Description of Related Art

For the energetic characterization of adsorbents on a gas-solid boundary surface, it is helpful to know the integral or respectively differential sorption enthalpies of the used gas-solid systems in addition to the sorption isotherms. In particular in the case of technical sorption processes, which occur in a non-isothermal manner in the gas phase almost without exception, this knowledge of the sorption heats is valuable since technical adsorbers represent quasi-adiabatic systems due to the relatively small surface-to-volume ratio.

Calorimeters can be based mainly on two different measurement processes. On the one hand, they can work according to the compensation principle, in which the heat tone to be measured is compensated for by an active heating or respectively cooling and the power necessary for this is detected. On the other hand, it can be based on the exchange principle, in which the heat flow generated by the heat tone leads to a temperature change between the sample and the surrounding area, which is detected.

Until now, on the one hand, microcalorimeters, which are typically equipped with a single sample cell, and secondly, dynamic difference calorimeters (DSC), which are operated with a sample cell and a reference cell arranged in a parallel manner, are available commercially. For technical and economic reasons, both types of calorimeters cannot be used for the simultaneous measurement of sorption isotherms and sorption enthalpy.

Technical literature contains isolated references to sorption calorimeters of scientific working groups, which almost exclusively concern apparatuses for laboratory experiments for university research that were developed and built internally by colleges/universities themselves. In general, we can differentiate between apparatuses for basic research, e.g. for examining bond enthalpies in the case of notably low surface assignment in a high vacuum, and apparatuses for the measurement of sorption and sorption enthalpy in procedurally relevant pressure and temperature ranges. The structure of the latter apparatuses is highly experimental, notably complex and thus very expensive. The conducting of measurements with these apparatuses is mainly manual due to the structure and functional principle of these apparatuses, is very involved and accordingly labor-intensive.

One of the biggest weaknesses of the currently existing apparatuses for the measurement of sorption and sorption enthalpy in procedurally relevant pressure and temperature ranges is that, in measuring mode, changes from external factors, device-specific changes as well as heat effects, caused by the change in the atmosphere in the measurement cells, cannot be taken into consideration. These heat effects can be, among other things, the heat input through a temperature of the supplied gaseous substance that is potentially different than the measurement cell or the heat received or respectively emitted during the expansion or respectively compression of the gaseous substance in the measurement cell. The evaluation of the data received with these measuring devices is also based on simplified models and different exceptions must be made for changes in the atmosphere inside the measurement cells, which leads to strong restrictions with respect to the accuracy of the obtained results.

Furthermore, these measuring devices lack the possibility of a reliable, fast and generally valid calibration, since, up until now, only a manual calibration has been possible, wherein a calibration must be performed before each individual measurement. This calibration is involved and reproducible values can only be obtained using these measuring devices with great effort, which are even then considerably less exact when compared with conventional calorimetry measurements and have many errors.

BRIEF SUMMARY OF THE INVENTION

The object of the invention is to provide a commercially usable and inexpensive device and a method with which a sorption enthalpy can be measured in a simple manner.

According to the invention the device for calorimetrically measuring sorption processes comprises a measuring cell for receiving a sample, here called the sorption cell, wherein the sorption cell has a volume to be filled with a sorption gas, and another measurement cell, here called the reference cell, likewise to be filled with the sorption gas. A measurement gas volume is arranged around the sorption cell for receiving a reference gas, for example nitrogen, air, carbon dioxide or one of the noble gases. Furthermore, the reference cell is surrounded by a reference gas volume, which is likewise provided for receiving the reference gas.

Furthermore, the device according to the invention comprises a gas connection between the sorption cell and the reference cell in order to conduct sorption gas into the sorption cell and the reference cell such that a sorption reaction occurs with the sample in the sorption cell. Furthermore, the device for calorimetric measurement according to the invention comprises a device for measuring pressure differences between the measurement gas volume and the reference gas volume in order to carry out a calorimetric measurement of the sorption process on the sample in the sorption cell on the basis of a volume change of the reference gas in the measurement gas volume during the measuring process.

In the case of the method for calorimetrically measuring sorption processes according to the invention, a sample is first added to a sorption cell. A sorption gas, the sorption onto the sample of which is to be calorimetrically measured, is then directed into the sorption cell and into a reference cell connected with it so that a sorption reaction with the sample results in the sorption cell, whereupon a calorimetric measurement of the sorption process is performed.

If heat is now released during the measurement in the sorption cell as a result of a sorption to the sample, then it flows into a measurement gas volume surrounding the sorption cell and there leads to a temporary heating of the gas. The resulting pressure increase is measured in comparison to the pressure in the reference gas volume by means of a device for difference pressure measurement. The pressure difference determined in this manner is proportional to the released heat during the sorption process. Since all heat flows and atmospheric changes not underlying the sorption occur not only in the sorption cell but also in the reference cell, such effects are intrinsically excluded from the obtained results in the case of the method based on the differential pressure of both measurement cells.

The complete compensation of the effects of the atmosphere overlying the measurement or respectively of the changes in the atmosphere during the measurement achievable through the structure with a sorption cell and a reference cell, which leads to a considerably increased measurement accuracy, is advantageous with respect to the state of the art. The effort for the measurement is thereby comparable to a conventional calorimetric measurement.

It is also advantageous that the measurement process is based on the recording of pressure differences between the gas volumes and not on the measurement of temperatures, temperature differences or heat output as in the state of the art, whereby a further significant increase in measurement accuracy is achieved.

The device for calorimetrically measuring sorption processes according to the invention comprises two measurement cells, a sorption cell and a reference cell. Both the measurement cells and the gas connection between the measurements are made of a gas-tight material, which behaves in a chemically inert manner with respect to the introduced sorption gas as well as with respect to the sample in an advantageous embodiment of the invention, which would lead to an atmospheric change, to additional heat flows and to a change in the chemical composition of the sorption gas.

Thereby for both measurement cells an inner volume of a few microliters up to several liters is thereby possible, preferably 10 µl to 0.1 l, particularly preferably 0.5 to 5 cm3.

The sample inside the sorption cell can be any solid, a gel or a liquid in the volume of which or on the surface of which a reaction takes place or respectively the introduced sorption gas is sorbed. The sorption gas can be any gaseous substance. Aerosols, i.e. liquid or solid substances dispersed in a gaseous medium, are also conceivable.

The reference cell is connected with the sorption cell to be filled with the sorption gas via the gas connection. During the measurement, the reference cell can only contain the sorption gas or there is the option of the additional filling with a sample, as is provided for the sorption cell.

A gas volume is respectively arranged around both measurement cells, wherein large portions of the sorption cell are preferably surrounded by the measurement gas volume and large portions of the reference cell by the reference gas volume and particularly preferably both measurement cells are surrounded completely and on all sides by the respective gas volumes—if applicable up to the supply lines. The greatest possible enclosure of the measurement cells by the gas volumes is advantageous since the most complete possible transfer of heat from the measurement cells into the gas volumes is ensured.

In another advantageous embodiment of the device, the distances measured orthogonally between all points of the surface of the respective measurement cell and the inner wall of the corresponding gas volume differ from other by no more than 20%, preferably no more than 10%; particularly preferably, the distances between the walls of the measurement cell and the gas volume surrounding it are the same size at all points so that the most even possible heat flow results inside the gas volume.

According to the invention, a gas connection is provided between the sorption cell and the reference cell. It can thereby be a simple line made of any material or even another component of the device, which interconnects directly or indirectly the interior spaces of both measurement cells.

Furthermore, the device according to the invention between the measurement gas volume and the reference gas volume comprises a device for measuring the pressure difference. The measuring of the pressure difference can take place for example by means of a differential pressure sensor, for example with a separation membrane, or by means of several sensors, for example piezoresistive, piezoelectric or capacitive pressure sensors.

The arrangement of the device for measuring the pressure difference at the measurement gas volume and the reference gas volume can take place directly or via additional components of the device. Thus, for example, it can also be connected with a part of a device for filling with the reference gas.

In an advantageous embodiment of the invention, the two measurement cells, the sorption cell and the reference cell, as well as the components connected with them are arranged as symmetrically as possible, preferably mirror-symmetrically, to a line, which runs parallel to a main axis of the measurement cells and/or centered between the two measurement cells and also goes particularly preferably through the middle point of the equipment, whereby the intrinsic compensation for all effects disrupting or falsifying the measurement caused by the double-celled structure of the device is promoted by the similar surroundings of the two measurement cells.

According to a particularly advantageous embodiment of the invention, one heating element is provided with an effective zone inside each of the sorption cell and the reference cell. The heating element can be any device for targeted heating, preferably comprising an electrical resistor element like a PTC or NTC resistor, particularly preferably a metallic resistor element made of platinum, such as a PT100 resistor element. The installation of electrical resistor elements in both measurement cells is advantageous due to the possibility of in-situ calibration of the calorimeter during the measuring process through regulated electrical heating of the resistor elements.

According to this embodiment of the invention, the heating element can be integrated into the wall of the measurement cells or can extend partially or completely into the inside of the respective measurement cell. In a particularly advantageous further embodiment of the invention, the heating element is thermally insulated with respect to the wall of the respective measurement cell so that the heat input by the heating element only takes place into the inside of the measurement cell but not directly onto the cell wall.

An identically constructed heating element is preferably located in each of the two measurement cells, the sorption cell and the reference cell.

The heating element can also preferably be used to capture the temperature respectively of the inside of the sorption and the reference cell. In one possible embodiment of the invention, this can also take place via an electrical and/or metallic resistor element, such as a PT100 resistor element.

It is also advantageous if the heating elements are each controllable separately from each other in the sorption cell and in the reference cell via a control unit so that a controlled, short-term heat input into each of the two measurement cells can take place independently of each other. By means of the control unit, the temperature in the measurement cells can also preferably be measured independently of each other by means of the respective heating element, whereby the temperatures can also be captured centrally and can both be included in the assessment of the measurement signal and can represent a part of the data that can be called by the user.

According to another advantageous embodiment of the invention, it is provided that a calibration of the device can be performed before, during and/or after the calorimetric measurement and, particularly preferably, this takes place fully automated.

In an advantageous further embodiment of the method, in-situ calibrations are performed once, repeatedly or continuously during the calorimetric measurement, wherein an in-situ calibration means a calibration at least under measurement conditions, preferably during the measurement process. A short-term, controlled heat input thereby takes place by means of one of the heating elements either in the sorption cell or in the reference cell, whereby an additional pressure difference can be observed between the gas volumes surrounding the measurement cells, which is proportional to introduced heat quantity. One advantage of these calibrations is that the recorded pressure increase can thus be recalculated into an absolute heat quantity after the measurement. This enables a direct determination of the sorption enthalpies from the heat conversion so that restrictions through models and exceptions are omitted. Since this calibration takes place under measurement conditions (among other things, temperature, gas pressure, atmosphere) with the sample in the sorption cell and can repeated as often as necessary during the measurement, all effects disrupting or falsifying the measurement, if applicable also in their temporal development during the measurement, are hereby advantageously taken into consideration, thus for example the (temporal) change in the heat capacity of the atmosphere in the sorption cell.

In another possible further embodiment of the method, a cross-calibration for determining device-specific variables takes place before or during the calorimetric measurement, wherein, by means of one respective heating element, alternately a short-term, controlled heating of the sorption cell and the reference cell is performed whereby respectively a pressure difference of the gas volumes surrounding the measurement cells occurs, which is proportional to the introduced heat quantity and has an identical proportionality factor in the case of full symmetry of the device for both measurement cells. If the device is not completely symmetrical, which can on the one hand have instrumentally caused reasons based on the general structure of the device but can also be based on the specific parameters of the respective measurement, for example through differences in the heat capacity of contents of the two measurement cells, then a respective correction factor can be calculated easily and, if desired, automatically, by means of the aforementioned further development of the method, consideration of which in the assessment of the measurement signal leads to considerably more exact and reproducible results. In the case of the known symmetry factor, a simple calibration with heat input into only one of the measurement cells may suffice.

Furthermore, it is possible to introduce a short-term, controlled, same-sized heat input simultaneously into the sorption cell and into the reference cell before or during the measurement by means of the heating elements, which should lead to no pressure difference in the two gas volumes in the case of complete symmetry of the calorimeter structure. A nonetheless-occurring pressure difference can also be used to calculate a correction factor in the assessment of the calorimetric measurement, which leads to more exact results in the assessment of the received measurement signal.

Alternatively or in addition to a calibration, a heating element, in particular a heating element arranged in the reference cell, can also be used directly for the measurement. This can take place for example in that a heat input via the heating element in the reference cell is specified as simultaneously as possible to the occurring sorption reaction in the measurement cell and a comparison of the heat quantities entering the gas volumes from the measurement cells takes place by means of pressure difference measurement.

In particular upon reaching equilibrium, for example a pressure difference of zero, i.e. the same heat input in both gas volumes, the heat quantity in the measurement cell can thus be determined based on the heat quantity specified in the heating element. In a concrete embodiment, it is for example possible to provide a regulator for the heat quantity supplied to the heating element, wherein the pressure difference is regulated to zero. The electrically supplied heat output is easily recordable and corresponds with the heat contribution to the sorption reaction, either directly or, if applicable, modified with a factor in the case of potential asymmetry.

In the case of a possible embodiment of the invention, the reference cell has mainly the same geometry as the sorption cell and/or the reference gas volume has mainly the same geometry as the measurement gas volume. This means that the sorption cell and the reference cell and/or the reference gas volume and the measurement gas volume preferably have a comparable geometric design and the surface of both measurement cells and/or both gas volumes differ from each other no more than 100%, preferably no more than 25%, particularly preferably no more than 5%.

In a particularly preferred advantageous embodiment of the invention, the sorption cell and the reference cell and/or the reference gas volume and the measurement gas volumes are at least mainly identical in their form, dimension and their material, which ensures the greatest possible comparability of the received data and a minimization of required corrections.

In a possible further embodiment of the invention, a blockable intake device is provided at least for the sorption cell, in order to fill the sorption cell with the sample and/or also with sorption gas. The reference cell can also have a blockable intake device in order to also be able to add a sample additionally or separately to the sorption cell, sorption gas or in another possible further embodiment of the invention. The blocking of the intake device can take place for example via one or more valves or gates, which can be operated manually, electrically, pneumatically or otherwise, or via a screwable or otherwise closable lock.

Furthermore, different embodiments of the invention are possible, in which a device for measuring the sorption gas pressure for measuring sorption isotherms is provided. This can take place via any pressure sensor, for example a piezoresistive, piezoelectric, capacitive or inductive pressure sensor. The device for measuring the sorption gas pressure can be located on any sorption-gas-filled component of the device for calorimetric measurement, preferably on the gas connected between the sorption cell and the reference cell or on a blockable intake device of the sorption cell or the reference cell. Through such a coupling of volumetrically working measurement processes with the calorimetry, the sorption isotherms and the charge-dependent sorption enthalpies can be measured simultaneously in a device. A far-reaching advantage of this coupling is the direct determination of sorption enthalpies from the heat conversion during the measurement so that restrictions through models and assumptions are omitted.

In the case of one possible embodiment of the invention, a blockable line for connecting the inside of the measurement gas volume and the reference gas volume is provided between the two volumes in order to establish pressure equalization. The blockable line can thereby be a separate component of the device or can be realized via additional components located in the device, for example as part of the device for pressure difference measurement or as part of the device for filling with reference gas. The blocking of the line can take place for example via one or more valves or gates, which can be operated manually, electrically, pneumatically or otherwise.

In an advantageous embodiment of the method, a simultaneous measurement of an sorption isotherm takes place during the calorimetric measurement by means of a device for measuring the sorption gas pressure located in the equipment or an externally attached measuring device connected with the sorption cell, whereby the time-dependent progression of the sorption gas pressure can take place and thus, among other things, information on the underlying sorption mechanism is received. Furthermore, in the case of this embodiment, it is advantageous that the calorimetric measurement and the recording of the sorption isotherms can only be performed simultaneously with one piece of equipment. This results in a reduction in time and financial investment, a reduction in the number of necessary measuring devices, which saves both space and maintenance costs, as well as the biggest advantage that the calorimetric measurement and the recorded sorption isotherms originate from the same process and not from a reproduction of the same process in another measuring device, wherein both measurements would be subject respectively to their own device-specific parameters.

BRIEF DESCRIPTION OF THE SEVERAL VIEWS OF THE DRAWINGS

Different exemplary embodiments of the invention are explained in greater detail below with reference to the drawings. The drawings show in.

DETAILED DESCRIPTION OF THE INVENTION

Figure 1:
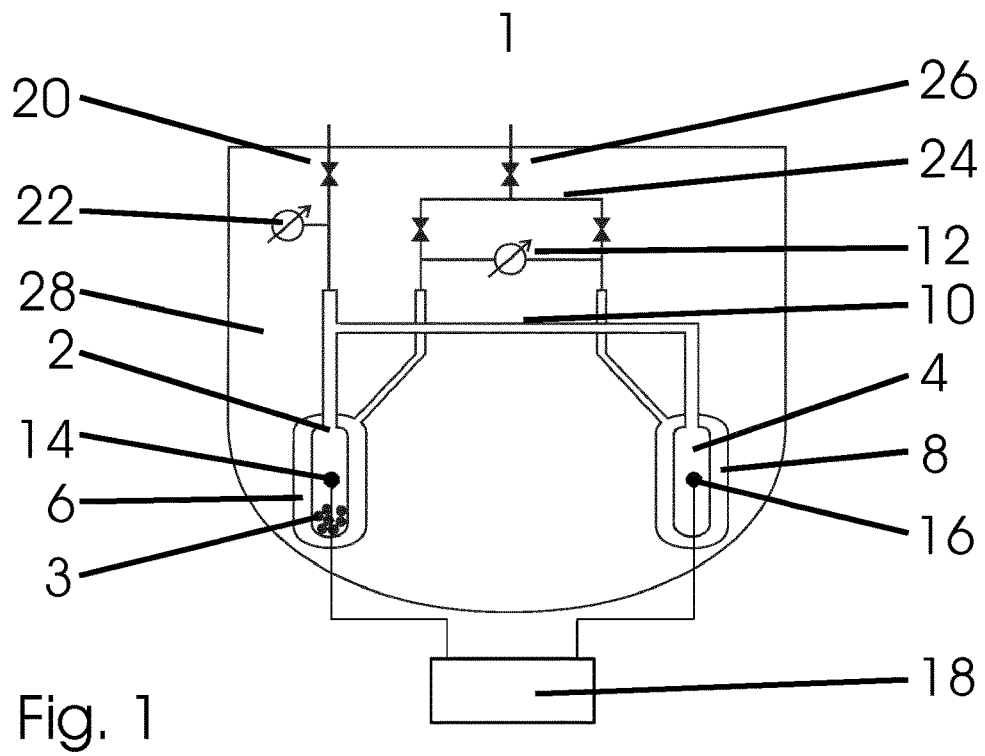
FIG. 1 a schematic representation of a first embodiment of the invention.

The first embodiment of a device 1 shown in FIG. 1 for calorimetrically measuring sorption processes has a sorption cell 2 for receiving a sample 3 as well as a reference cell 4, wherein the sorption cell 2 and the reference cell 4 are arranged symmetrically with respect to each other inside the device 1.

Respectively one gas connection 10 is arranged on the upper end of the sorption cell 2 and the reference cell 4, which connects the interior spaces of the both measurement cells 2, 4 so that sorption gas can be conducted simultaneously to both measurement cells 2, 4 and there is a pressure equalization in both measurement cells 2, 4.

The sorption gas is introduced via a supply line with shut-off valve 20, which leads along the main axis of the sorption cell 2 from inside the device 1 to the outside and is connected with the gas connection 10 above the sorption cell 2. The valve arranged on the upper end of the supply line with shut-off valve 20 seals the equipment in a gas-tight manner and serves to fill the sorption cell 2 and the reference cell 4 with sorption gas. An inlet, for example a releasable pipe connection, through which a sample 3 can be added to the sorption cell 2, is not shown in the schematic representation of FIG. 1.

The pressure of the sorption gas inside the sorption cell 2 and the reference cell 4 is measured by means of a precision pressure transducer 22, which is located above the sorption cell 2 connected with the supply line with shut-off valve 20 inside the device 1.

The sorption cell 2 is—except for the supply line—completely surrounded by a measurement gas volume 6, which is filled with a reference gas, e.g. argon. The reference cell 4 is surrounded by a reference gas volume 8, which is also filled with the reference gas and designed in its form identical to the measurement gas volume 6. Lines are arranged in the upper area of both gas volumes 6, 8, each of which lead to one side to a differential pressure sensor 12 arranged between the measurement gas volume 6 and the reference gas volume 8.

Another line 24 with two gas-tight valves is connected with the lines leading from the two gas volumes 6, 8 to the differential pressure sensor 12 and arranged parallel to the differential pressure sensor 12. A device for filling with reference gas 26 is arranged centered between these two valves and connected directly with the line 24, which consists of a simple line with a valve in the embodiment sketched in FIG. 1. With the help of the valves of the device for filling with reference gas 26 as well as the two valves arranged on the line 24, reference gas can be added both to one or both of the gas volumes 6, 8 and a pressure equalization between the measurement gas volume 6 and the reference gas volume 8 can also be realized.

Respectively one heating element 14, 16 for short-term introduction of a defined heat quantity into the inside of the respective measurement cell 2, 4 is located respectively centered inside the sorption cell 2 and the reference cell 4. The heating elements 14, 16 shown here are electrical resistor elements, each of which are connected with a cable, which leads out of the measurement cell 2, 4 through the gas volume 6, 8 arranged around it to a control unit 18 located outside the device 1. The control unit 18 regulates both the heating as well as the recording of the temperature of the inside of the sorption cell 2 and the reference cell 4 respectively separately from each other by means of the electrical resistor elements 14, 16.

All structural elements of the device 1 for calorimetrically measuring sorption processes shown in FIG. 1, except for the control unit 18, are located inside an insulated, thermostaticized vessel 28, which thermally insulates the structural elements of the device 1 arranged on its inside with respect to the surroundings.

The vessel 28 can be for example an evacuated vacuum housing, a liquid-filled vessel, which is brought to the right temperature in a regulated manner by means of a thermostat arranged internally or externally or a suitable thermal insulation vessel.

A sample 3 is first added to the sorption cell 2 in order to perform a calorimetric measurement of a sorption process.

The sample 3 is first prepared for the measurement and thereby pretreated, if applicable. The volume of the measurement cell 2 and thus also the volume of the reference cell 4 is then either supplied with a defined gas at a predetermined pressure or—preferably—evacuated.

A calibration then takes place automatically. In the case of the known asynchrony factor, this can take place as a simple calibration, but a cross-calibration for determining device-specific variables is preferred, wherein a short-term, regulated heating of the sorption cell 2 and the reference cell 4 takes place by means of respectively one electrical resistor heating element 14, 16 in an alternating manner, whereby respectively a pressure difference of the gas volumes 6, 8 surrounding the measurement cells 2, 4 occurs, which is proportional to the added heat quantity and has an identical proportionality factor in the case of the complete symmetry of the device for both measurement cells 2, 4. If the device 1 is not completely symmetrical, which can on the one hand have instrumentally caused reasons based on the general structure of the device 1 but can also be based on the specific parameters of the respective measurement, for example through differences in the heat capacity of contents of the two measurement cells 2, 4, then a correction factor can be calculated automatically by means of the cross-calibration, which is taken into consideration in the later assessment of the measurement signal.

A sorption gas, the sorption onto the sample 3 of which is to be examined calorimetrically, is then directed into the sorption cell 2 and into a reference cell 4 connected with it so that a sorption reaction with the sample 3 results in the sorption cell 2, whereupon a calorimetric measurement of the sorption process is performed. If applicable, another cross-calibration is performed at the beginning or during the calorimetric measurement according to the method described above.

If heat is now released during the measurement in the sorption cell 2 as a result of a sorption to the sample 3, then it flows into a measurement gas volume 6 surrounding the sorption cell 2, whereas a sorption of the sorption gas does not result in the reference cell 4 and as a result there is also no sorption-caused heat flow into a reference gas volume 8 surrounding the reference cell 4. The additional heat flow into the measurement gas volume 6 leads to a temporary heating of the gas inside and thus to a pressure increase, which first rises sharply over time and then drops slowly again until finally the thermal equilibrium in the entire system is reached again and a pressure difference is no longer registered between the two gas volumes 6, 8. In the reference gas volume, there is no pressure increase due to the sorption process during the entire process. The pressure increase in the measurement gas volume 6 is measured by means of the differential pressure sensor 12 in comparison to the pressure in the reference gas volume 8. The pressure difference determined in this manner is proportional to the released heat during the sorption process. Since all heat flows and atmospheric changes not underlying the sorption occur not only in the sorption cell 2 but also in the reference cell 8, such effects are intrinsically excluded from the obtained result in the case of the method based on the differential pressure of both cells.

The measurement of the heat quantity takes place based on the observation of the peak of the resulting temporal progression of the pressure difference, using the previous or subsequent calibration, from which the connection between the pressure difference and the heat input is known. In-situ calibrations can thereby be performed repeatedly or continuously during the calorimetric measurement, wherein a short-term, regulated heat input occurs by means of an electric resistor heating element 14, 16 either in the sorption cell 2 or in the reference cell 4, whereby an additional pressure difference between the gas volumes 6, 8 surrounding the measurement cells 2, 4 can be observed, which is proportional to the introduced heat quantity, whereby the recorded pressure increase after the measurement can be recalculated directly into an absolute heat quantity.

Particularly preferred is a multi-step measurement with consecutive measurement steps with the gradually increasing pressure of the sorption gas. The measurement cell and the reference cell are hereby first evacuated and then a first calibration is performed as a cross-calibration or a simple calibration. The sorption gas is then let into the measurement cells 2, 4 at a defined, low pressure level and the described calorimetric measurement is performed through observation of the pressure difference. If we now wait until a thermally stable state sets in again after the subsiding of the initial peak, then a new in-situ calibration can subsequently take place in this stable state. The uniqueness is that the calibration is possible with the exact measurement conditions and thus the impacts of errors such as changing heat capacities are taken into consideration in the calibration.

Afterwards additional sorption gas is supplied in another measurement step and the measurement is repeated at a second, higher pressure level, including the subsequent calibration. A continuation with additional measurement steps with respectively increasing pressure is possible.

Figure 2:
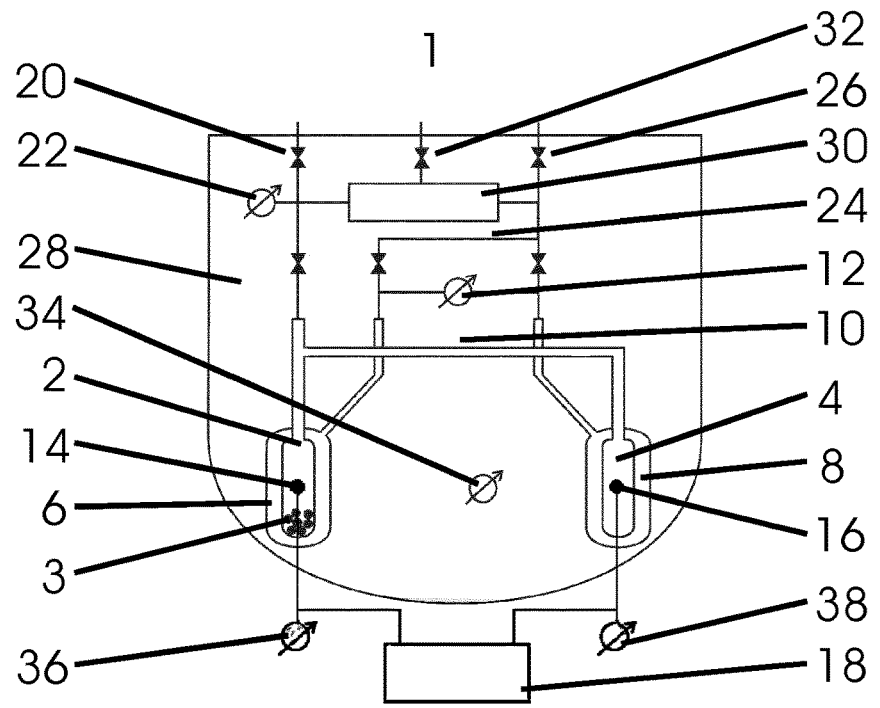
FIG. 2 a schematic representation of a second embodiment of the invention.

FIG. 2 shows a schematic representation of another possible embodiment of a device 1 for calorimetrically measuring sorption processes. Its basic elements are the same as those in the embodiment shown in FIG. 1, but it is enhanced by a series of structural elements.

With respect to the embodiment shown in FIG. 1, the device 1 in FIG. 2 is enhanced by a gas storage tank 30, which is connected with the supply line with shut-off valve 20 as well as the device for filling with reference gas 26 in the upper part of the device 1. The pressure inside the gas storage tank 30 can be measured via the precision pressure transducer 22 connected with it via a line.

A blockable inlet 32 is arranged directly on the gas storage tank 30, by means of which the gas storage tank 30 can be both evacuated and filled. The gas storage tank can both be filled with reference gas both via the device for filling with reference gas 26 and with sorption gas via the supply line with shut-off valve 20.

Both the line from the gas storage tank 30 to the sorption cell 2 as well as the line from the gas storage tank 30 to the measurement gas volume 6 and the reference gas volume 8 are blockable via valves, wherein in the second case the valves are part of the blockable line 24.

In this embodiment of the invention, the gas storage tank 30 represents a central component with which all three intake devices, the device for filling with reference gas 26, the supply line with shut-off valve 20 and the blockable inlet 32 are connected.

Furthermore, the exemplary embodiment shown in FIG. 2 has a temperature measuring device 34 inside the adiabatic vessel 28 for recording the temperature of a liquid or gaseous medium located in it.

Furthermore, in the exemplary embodiment of the device 1 in FIG. 2, a temperature measuring device 36, 38 is respectively connected with each of the two heating elements 14, 16, which are arranged inside the sorption cell 2 and the reference cell 4 for direct recording and rendering of the temperature during the measuring process.

Figure 3:
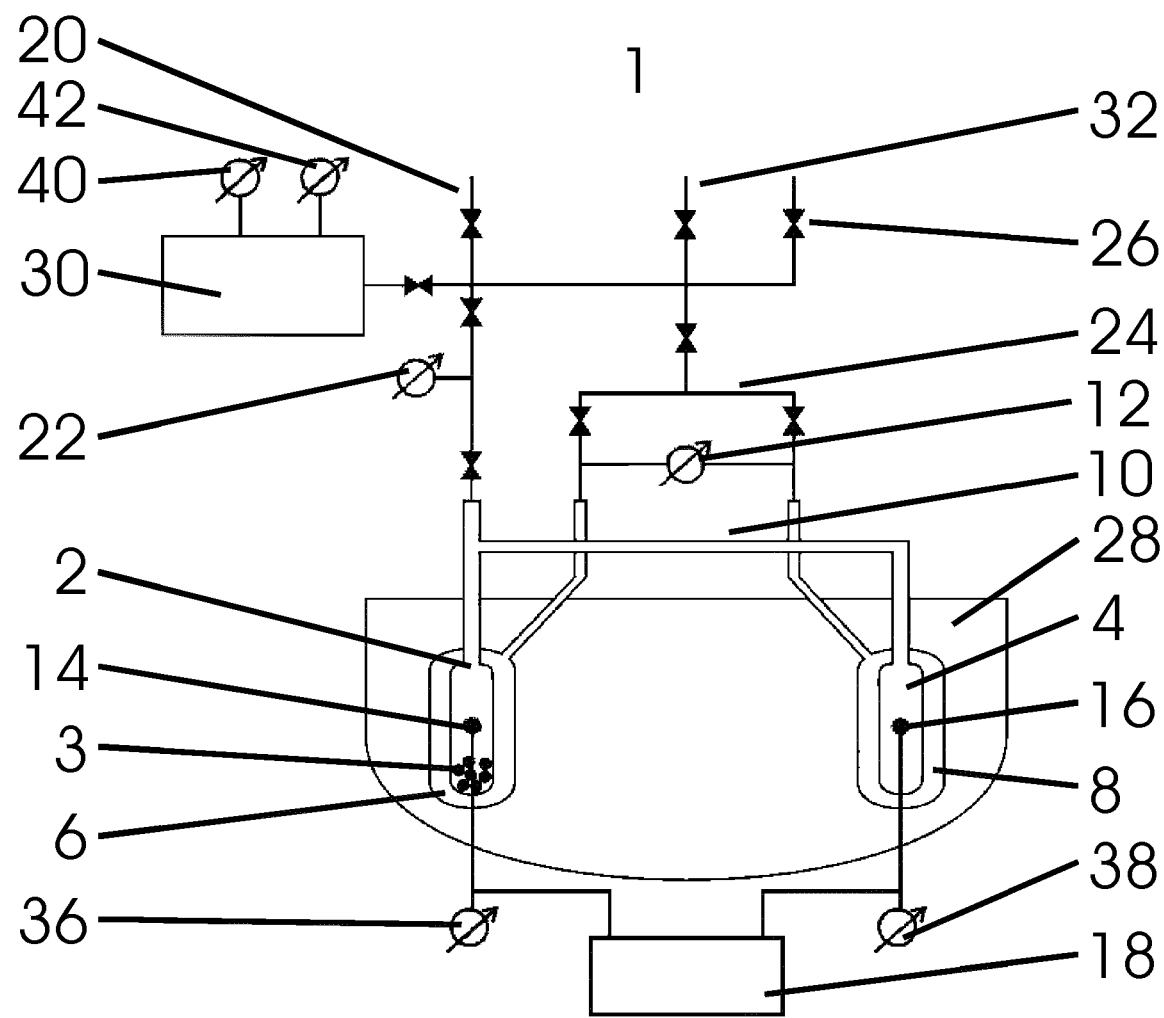
FIG. 3 a schematic representation of a third embodiment of the invention.

FIG. 3 shows a third embodiment of the invention. In the subsequent description, only the differences to the embodiment of the device 1 shown in FIG. 1 are covered.

The device 1 for calorimetrically measuring sorption processes shown here has a gas storage tank 30, which is connected in a blockable manner with respect to the rest of the device 1 by means of a line with a valve. A pressure measuring device 40 and a temperature measuring device 42 of the gas storage tank are arranged on the gas storage tank 30.

The supply line with shut-off valve 20, the device for filling with reference gas 26 and the blockable inlet 32 are connected with the gas storage tank 30 via a line in a blockable way. Starting from this line, two additional blockable lines lead to the sorption cell 2 and to the measurement gas volume 6 as well as to the reference gas volume 8.

Another difference to the embodiments shown above is the volume of the adiabatic vessel 28. In this embodiment of the invention, it no longer includes the entire device 1, but rather only the sorption cell 2 with the measurement gas volume 6 surrounding it as well as the reference cell 4 with the reference gas volume 8 surrounding it. The gas connection 10 between the gas volumes 6, 8, the differential pressure sensor 12, the precision pressure transducer 22 and the blockable line 24, as well as the gas storage tank 30 are located outside of the adiabatic vessel 28.

We claim:

1. A device for calorimetrically measuring a sorption reactions, comprising:
    a sorption cell for receiving a sample and having a volume to receive a sorption gas;
    a reference cell having a volume to receive the sorption gas;
    a measurement gas container surrounding the sorption cell and having a volume for receiving a reference gas;
    a reference gas container surrounding the reference cell and having a volume for receiving the reference gas;
    a gas connection disposed between the sorption cell and the reference cell and fluidically coupling the volumes of the sorption cell and the reference cell;
    a differential pressure sensor coupled to the measurement gas container and the reference gas container to determine a pressure difference there between that is proportional to heat released in a sorption reaction between the sorption gas and the sample; and
    a control unit in communication with the sorption cell, the reference cell and the differential pressure sensor, the control unit configured for determination of the heat released in the sorption reaction based on a pressure difference measured by the differential pressure sensor.

2. The device according to claim 1, wherein
a first heating element is disposed inside the sorption cell and a second heating element is disposed inside the reference cell.

3. The device according to claim 2, wherein
the first and second heating elements are regulated separately by means of the control unit for both the sorption cell and the reference cell.

4. The device according to claim 2, wherein
the first heating element is used to record the temperature of the inside of the sorption cell and the second heating element is used to record the temperature of the inside of the reference cell.

5. The device according to claim 2, wherein
each of the first and second heating elements comprises an electrical resistor element.

6. The device according to claim 3, wherein
the control unit performs a calibration, which takes place by means of an alternating or simultaneous short-term, regulated heating of the sorption cell and/or the reference cell.

7. The device according to claim 1, wherein
the reference cell has a same geometry as the sorption cell.

8. The device according to claim 1, wherein
an intake device is provided for filling of the sorption cell and/or the reference cell.

9. The device according to claim 1, wherein
the reference gas container has a same geometry as the measurement gas container.

10. The device according to claim 1, wherein
a line for connecting the inside of the measurement gas container and the reference gas container is provided for equalizing the pressure.

* * * * *

UNITED STATES PATENT AND TRADEMARK OFFICE
CERTIFICATE OF CORRECTION

PATENT NO. : 10,605,753 B2
APPLICATION NO. : 14/381946
DATED : March 31, 2020
INVENTOR(S) : Dieter Bathen et al.

Page 1 of 1

It is certified that error appears in the above-identified patent and that said Letters Patent is hereby corrected as shown below:

In the Claims

Column 11, Line 19 (Claim 1):
• Replace the word "reactions" with the word "reaction"

Signed and Sealed this
Eighteenth Day of August, 2020

Andrei Iancu
*Director of the United States Patent and Trademark Office*